United States Patent [19]

Harjunmaa et al.

[11] Patent Number: 5,183,042
[45] Date of Patent: Feb. 2, 1993

[54] ELECTROMAGNETIC METHOD AND APPARATUS TO MEASURE CONSTITUENTS OF HUMAN OR ANIMAL TISSUE

[75] Inventors: Hannu Harjunmaa, Holden; Yitzhak Mendelson; Yi Wang, both of Worcester, all of Mass.

[73] Assignee: Vivascan Corporation, Southboro, Mass.

[21] Appl. No.: 725,502

[22] Filed: Jul. 3, 1991

Related U.S. Application Data

[63] Continuation-in-part of Ser. No. 527,514, May 23, 1990, Pat. No. 5,099,123, which is a continuation-in-part of Ser. No. 511,229, Apr. 19, 1990, Pat. No. 5,137,023, which is a continuation-in-part of Ser. No. 511,341, Apr. 19, 1990, Pat. No. 5,112,124.

[30] Foreign Application Priority Data

May 23, 1989 [EP] European Pat. Off. ........ 89810382.5

[51] Int. Cl.⁵ .................... A61B 5/00; G01N 21/59
[52] U.S. Cl. .................................. 128/633; 356/39
[58] Field of Search ..................... 128/633–634, 128/664; 356/41, 39; 250/339, 341, 351, 352

[56] References Cited

U.S. PATENT DOCUMENTS

| | | |
|---|---|---|
| 1,758,088 | 5/1930 | Schmick . |
| 2,721,942 | 10/1955 | Friel et al. ............... 250/435 |
| 3,463,142 | 8/1969 | Harte ....................... 128/633 |
| 3,614,450 | 10/1971 | Hill et al. ................ 250/210 |
| 3,638,640 | 2/1972 | Shaw ......................... 356/41 |
| 3,926,527 | 12/1975 | Pembrook et al. ...... 356/246 |
| 3,958,560 | 5/1976 | March ....................... 356/39 |
| 3,963,019 | 6/1976 | Quandt ...................... 356/39 |
| 4,029,085 | 6/1977 | Dewitt et al. ............ 128/2 R |
| 4,033,330 | 7/1977 | Willis et al. ............... 356/39 |
| 4,169,676 | 10/1979 | Kaiser ...................... 128/633 |
| 4,266,554 | 5/1981 | Hamaguri ................ 128/633 |
| 4,267,844 | 5/1981 | Yamanishi ............... 128/633 |
| 4,306,877 | 12/1981 | Lubbers ................... 23/230 R |
| 4,321,930 | 3/1982 | Jobsis et al. ............. 128/633 |
| 4,380,240 | 4/1983 | Jobsis et al. ............. 128/633 |
| 4,398,541 | 8/1983 | Pugliese .................. 128/665 |
| 4,427,889 | 1/1984 | Muller ..................... 250/339 |

(List continued on next page.)

FOREIGN PATENT DOCUMENTS

| | | |
|---|---|---|
| 0074428 | 3/1983 | Fed. Rep. of Germany . |
| 0407992 | 1/1991 | Japan . |
| 0152979 | 8/1985 | Netherlands . |
| PCT/US90/00394 | 1/1990 | PCT Int'l Appl. . |
| 0160768 | 4/1984 | Switzerland . |

OTHER PUBLICATIONS

R. A. Peura and Y. Mendelson, "Blood Glucose Sensors: An Overview", IEEE/NSF Symposium on Biosensors, pp. 63–68 (1984).
Ser. No. 511,341, filed Apr. 19, 1991, to Harjunmaa et al.
Ser. No. 511,229, filed Apr. 19, 1991, to Mendelson et al.
Ser. No. 527,514, filed May 23, 1990, to Harjunmaa et al.

Primary Examiner—Lee S. Cohen
Assistant Examiner—Kevin Pontius
Attorney, Agent, or Firm—Hamilton, Brook, Smith & Reynolds

[57] ABSTRACT

To deterine glucose or other constituents of the human or animal body, near-infrared radiation containing two alternating wavelengths that have equal extinction coefficients in the tissue is directed onto a sample area of the body. The intensity relation of the two different wavelengths is adjusted so as to balance the two wavelength detected signals. The extracellular-to-intracellular fluid ratio of the tissue is changed or is allowed to change, and the alternating component of the transmitted beam power is measured. The amplitude of the alternating-current (AC) signal given by the detector represents glucose concentration or the difference from a preset reference concentration.

28 Claims, 2 Drawing Sheets

U.S. PATENT DOCUMENTS

| | | | |
|---|---|---|---|
| 4,485,820 | 12/1984 | Flower | 128/633 |
| 4,490,845 | 12/1984 | Steinbruegge et al. | 250/210 |
| 4,513,751 | 4/1985 | Abe et al. | 128/2 R |
| 4,570,638 | 2/1986 | Stoddart et al. | 128/665 |
| 4,586,513 | 5/1986 | Hamagur | 125/633 |
| 4,603,700 | 8/1986 | Nichols et al. | 128/633 |
| 4,621,643 | 11/1986 | New, Jr. et al. | 128/633 |
| 4,653,498 | 3/1987 | New, Jr. et al. | 128/633 |
| 4,655,225 | 4/1987 | Dahne et al. | 128/633 |
| 4,704,029 | 11/1987 | Van Heuvelan | 356/39 |
| 4,725,147 | 2/1988 | Stoddart | 356/433 |
| 4,750,496 | 6/1988 | Reinhart et al. | 128/635 |
| 4,759,369 | 7/1988 | Taylor | 128/633 |
| 4,768,516 | 9/1988 | Stoddart et al. | 128/665 |
| 4,796,636 | 1/1989 | Branstetter et al. | 128/33 |
| 4,805,623 | 2/1989 | Jobsis | 128/633 |
| 4,817,623 | 4/1989 | Stoddart et al. | 128/665 |
| 4,832,484 | 5/1989 | Aoyagi et al. | 356/41 |
| 4,863,265 | 9/1989 | Flower et al. | 356/41 |
| 4,882,492 | 11/1989 | Schlager | 250/346 |
| 5,028,787 | 7/1991 | Rosenthal et al. | 250/341 |

ELECTROMAGNETIC METHOD AND APPARATUS TO MEASURE CONSTITUENTS OF HUMAN OR ANIMAL TISSUE

RELATED APPLICATIONS

This is a continuation-in-part of co-pending application U.S. Ser. No. 07/527,514 filed May 23, 1990, now U.S. Pat. No. 5,099,123 entitled "Method for Determining by Absorption of Radiations the Concentration of Substances in Absorbing and Turbid Matrices" claiming priority to EPA 89810382.5 filed May 23, 1989, and U.S. Ser. No. 07/511,229 filed Apr. 19, 1990, now U.S. Pat. No. 5,137,023 entitled "Method and Apparatus for Monitoring Blood Analytes Noninvasively by Pulsatile Photoplethysmography", and U.S. Ser. No. 07/511,341 filed Apr. 19, 1990, now U.S. Pat. No. 5,112,124 entitled "Measuring the Concentration of Absorbing Substances".

Also, a U.S. patent application 5,178,142 entitled "Electromagnetic Method and Apparatus to Measure Constituents of Human or Animal Tissue" has been filed concurrent with this application. All of the above-referenced patent applications are hereby incorporated by reference.

BACKGROUND OF THE INVENTION

This invention relates to the non-invasive measurement of the concentration of substances that absorb electromagnetic radiation, such as light or infrared radiation, in absorbing and turbid matrices, such as human or animal body tissue, using a probe beam of electromagnetic radiation. The invention is described as applied to the special case of glucose measurement in human tissue using near-infrared radiation. It is, however, generally applicable to measurements of the concentration of any species that absorbs electromagnetic radiation, especially in strongly absorbing and turbid matrices.

The infrared measurement methods known in the art are not well adapted to the problem of quantifying an analyte dissolved in a strongly absorbing solvent. The known methods include separate or directly alternating measurements at a "glucose" wavelength and at a "reference" wavelength, where glucose does not absorb, as well as differential wavelength modulation about a glucose absorption band (C. Dahne, D. Gross, European Pat. No. 0 160 768 and references therein). In the known methods, the signal is easily lost into the variable and strong background presented by water and other constituents in the tissue and in the capillary blood flow.

SUMMARY OF THE INVENTION

The present invention is an improvement over co-pending European patent application No. 9810382.5 (Harjunmaa), U.S. Ser. No. 07/527,514 referenced above. In Harjunmaa, a balanced differential modulation method is disclosed wherein a radiation beam comprised of alternating pulses of two wavelengths forming a combined beam, is balanced or nulled using a reference detector that takes a sample of the combined beam before it enters the tissue and is detected by a primary detector. Although suitable for the purposes intended, the precautions taken to deal with the unavoidable differences in the spectral response between the reference detector and the primary detector make the system somewhat complicated.

The balanced differential (or balanced bridge) method of Harjunmaa utilizes two wavelengths that have the special property of having identical extinction coefficients in the sample matrix. A radiation beam is generated that contains these two wavelengths in alternate succession at a suitable frequency. When the beam is properly balanced for the measurement, a detector placed to detect the radiation beam does not detect any alternating component in the radiation. When the sample is inserted into the beam path, the same detector also would detect no alternating component, if the matrix did not contain any of the analytes. Only in the case where there is some analyte in the sample matrix will the detector detect an alternating signal synchronous with the wavelength alternation. This feeble alternating signal is amplified by many orders of magnitude and is then detected using a phase-sensitive detector (or lock-in amplifier).

In the method and apparatus of the present invention, the concentration measurement is accomplished using a two-wavelength alternating radiation beam which interacts with the tissue. The first wavelength is absorbed by the analyte whose concentration is being sought. The second wavelength has the same background extinction coefficient. Detected signals from the probe beam after passing through the matrix are balanced or nulled with a given unknown reference concentration of analyte present. Next, the fluid balance of the tissue in the radiation beam is changed thereby changing the ratio of the analyte concentration to the reference concentration. The alternating component of the interacted probe beam is then detected. The amplitude of the alternating-current (AC) signal given by the detector represents analyte concentration, or the difference from a preset reference analyte concentration. The interaction of radiation with tissue can occur in either a reflecting or transmissive mode.

DETAILED DESCRIPTION OF THE INVENTION

In the case of glucose determination in a human subject, it is known that, whereas extracellular fluid, which includes interstitial fluid and blood, has a certain glucose concentration, intracellular fluid contains very little glucose, since the latter is consumed inside the cells. Changing the ratio of extracellular to intracellular fluid in the path of a radiative brake beam thus provides a means to modulate the average glucose concentration seen by the beam as it propagates through the tissue. The fluid ratio can be changed by allowing the natural pulsation act on the tissue, or by artificial means, such as squeezing the tissue either between the transmitter and receiver parts of a measuring head (in the transmission mode), or between a combined transmitter-receiver and a suitable bone within the body, such as the forehead or the backside of the hand (in the reflection mode).

The purpose of the fluid ratio change is to provide for an initial intensity balancing with the tissue background included. Then an imbalance reading is taken from an incremental quantity of tissue, which is mostly blood, since blood is most easily displaced within the tissue. In the case of a transmission-mode measurement, the change of thickness can be either positive or negative. A positive change, or a thickness increase, is preferred, because in that case, the balancing can be done under conditions of a larger signal-to-noise ratio, as more transmitted power is available when the thickness is smaller.

Balancing with the same detector that is used to detect the actual measurement signal and with the tissue sample already in the radiation beam, cancels errors due to the two skin surfaces, most of the tissue in the radiation path, and those errors due to changes in the lamp spectral brightness and in the detector spectral sensitivity. The balancing accomplished in accordance with this invention also cancels the errors due to the fact that measurements made at different times, although intended to be made at exactly the same measuring site are, in practice, made at slightly different sites. The method according to this invention is sensitive only to the variable component of the tissue as its thickness is changed. This tissue is mostly blood and some interstitial fluid, which are more consistent in composition at different measuring sites. For this method to achieve good reproducible results, however, it is necessary that the aforementioned errors remain unchanged during the measurement.

Figure 1:
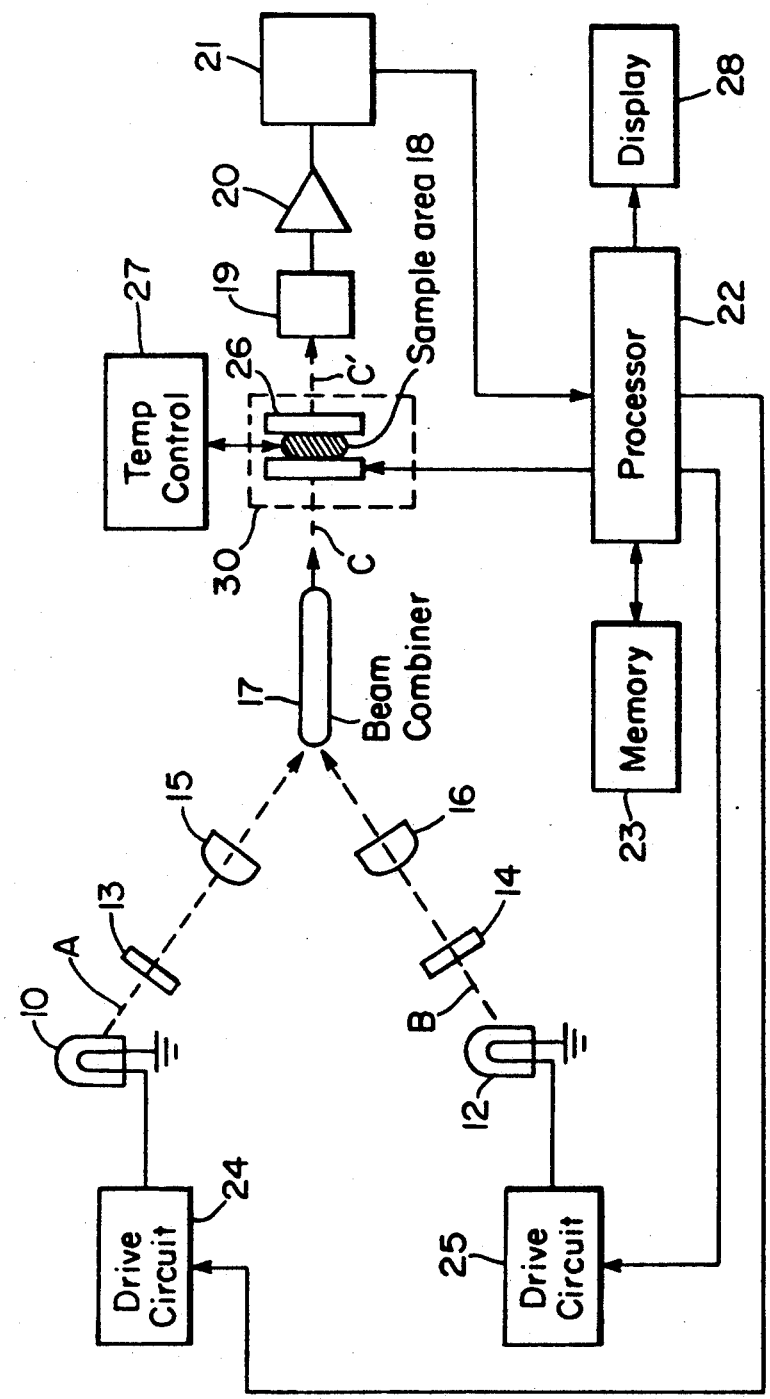
FIG. 1 is a block diagram of the apparatus of the invention.

Referring now to FIG. 1, the invention will be described in detail.

A pair of light sources 10 and 12 provide separate beams of light A and B. Sources 10 and 12 may comprise incandescent lamps capable of being intensity modulated in a rapid manner by drive circuits 24 and 25, which control the filament voltage applied to the lamps.

One of the lamps is called the master lamp 1 and the other is called the slave lamp 2, because the former is operated at a constant pulse brightness and the other is run at a brightness that balances the beam constituent intensities. In other words, the detected signals produced by beams A and B are made equal by adjusting the brightness of the slave lamp 12. The modulation frequency is preferably about 20 Hz, but could be anywhere between about 1 Hz and 1 MHz without changing the essence of this invention.

For the preferred embodiment, wavelengths of 2155 nm and 2272 nm are used and the system is operated in a transmissive mode.

The two required wavelengths are obtained by filtering the outputs of the two lamps 10 and 12 with interference filters 13 and 14, respectively. In this embodiment, the 2155 nm wavelength is selected from beam A and the 2272 nm wavelength is taken from beam B. The system would work equally well if this choice were reversed. Optical components known in the art, such as lenses 15 and 16, respectively, are used to direct the beams to a beam combiner 17, where the two substantially monochromatic beams are optically combined or time multiplexed together into a single beam.

The combined beam C is directed at, and enters the sampling area 18 of the body, such as a fingerweb or an earlobe.

After passing through the sample area 18, the attenuated beam C' is optically coupled to detector 19, which converts the optical intensity of beam C' to a corresponding AC electrical signal in which the amplitude of the AC signal corresponds to the difference between the intensities of beams A and E. Detector 19 preferably comprises a photoconductive lead sulfide (PbS) infrared detector operating at room temperature. The PbS detector is operated in a bolometer circuit and AC-coupled to a preamplifier 20. The preamplifier amplifies the detected AC analog signal from detector 19. The amplified AC signal is coupled to a conversion circuit 21 circuitry of a phase sensitive rectifier which produces analog DC signals of amplitude and polarity proportional to the amplitude and phase of the detected AC signal, and an A-D converter which produces a digital signal proportional to the analog signal.

The conversion circuit 21 is connected to a processor 22. The processor has at its disposal a memory 23 and a display unit 28 for storing and displaying, respectively, the digital signal. The processor also controls drive circuits for the two lamps 24 and 25.

In this example, the measurement is performed on a fingerweb. For that purpose there is provided a variable-gap mechanism 26 where the fingerweb is inserted for measurement. A temperature controller 27 is provided to standardize the temperature of the fingerweb and to keep constant the temperature of the measurement compartment.

A measurement is performed in the following way: The fingerweb is introduced between the gap mechanism 26. The mechanism gently squeezes the web, reducing the thickness of the tissue in the optical path. The master lamp 10 is modulated in a square wave mode, while the slave lamp 12 remains off. The square-wave signal produced by the detector 19 is monitored by the processor 22 through the digital signal from circuit 21. When the digital signal reaches a predetermined target amplitude, the squeezing stops. To avoid hurting the subject, there is a preset minimum thickness and a preset maximum pressure at which the squeezing stops even if the target amplitude has not been reached.

The processor records the amplitude by storing the digital signal into the memory 23.

Next, while the master lamp 10 is driven in a square-wave mode, the slave lamp 2 is switched on in a square-wave mode in antiphase with the modulation of the master lamp. Consequently, the square-wave signal produced by the detector 19 diminishes. The processor 22 monitors the amplitude of the digital signal from circuit 21 and increases the square-wave drive current of the slave lamp 12 until the digital signal from circuit 21 indicates a substantially zero amplitude. This process includes increasing the sensitivity of the conversion circuit by a factor of typically one thousand.

The amplitude of any residual square-wave signal is recorded. A residual signal may arise because the digital control circuit 25 used to adjust the intensity of the slave lamp has a finite resolution.

Under processor command, the adjustable gap mechanism 26 now releases pressure on the fingerweb increasing the thickness of tissue in the optical beam path by a predetermined amount. The material added into the beam path is mostly blood. The optimum thickness increase depends on the wavelengths used. Preferably, it is equal to one attenuation length in the added tissue. The "attenuation length" is the length of tissue beam punctuation at which the power of the radiation beam C is attenuated to 0.368 times its original value.

The amplitude of the detected square-wave signal is changed by the increase in the tissue thickness. The maximum change is obtained with a thickness change of one attenuation length. The amplitude change is caused by the differential absorbance of the body constituents at the two wavelengths used, and is thus proportional to the concentration of the component(s) that absorb differentially at the wavelengths used. For glucose determination, the wavelengths chosen are, in this embodiment, 2155 and 2272 nm, since at these wavelengths, the differential absorption of water and proteins is simultaneously small.

The processor 22 now calculates the glucose content by subtracting the residual digital signal from the digital signal obtained after the thickness increase and dividing the difference by the amplitude of the signal obtained with only the master lamp in operation. A previously determined proportionality constant is applied to the resultant term. Also, if necessary, a correction term obtained from a personal calibration step described below is also factored in. The result is displayed on the display unit 28.

The variable-gap mechanism housing 30 is temperature-controlled by the temperature control unit 27, so as to stabilize the tissue at a constant and known temperature of, for instance, 37 degrees Celsius.

As explained in Harjunmaa above, the signal obtained in a balanced differential measurement, when taken as a function of the path length in the sample, has a maximum value at a certain path length, which turns out to be the inverse of the extinction coefficient of the sample matrix. The extinction coefficient is the sum of the absorption and scattering coefficients. At wavelengths over 2000 nm, water absorbs so strongly that the optimum thickness is much less than 1 mm, a thickness difficult to obtain by squeezing any part of the human body without causing pain. The incremental balanced differential modulation method invented here makes it possible to obtain a maximal signal by letting the thickness increment be equal to the optimum path length, while at the same time, using a total sample thickness more comfortable to the subject. Also, as the absorption coefficient may be different for different tests that have to be carried out at different wavelengths, it is easy to vary the thickness increment accordingly.

It is noted that scattering by tissue is, at these wavelengths, comparable in magnitude to absorption as an extinction mechanism and causes the resultant extinction coefficient to be much larger than the water absorption coefficient alone.

The use of optical fiber to connect a movable measuring head to the instrument is made possible by the method of this invention. The fiber would replace the beam combiner 17 of FIG. 1. As the method relies on precise balancing of optical powers at two wavelengths, it is sensitive to differential changes in the transmittance of the system over the wavelength range, the type of difficulties a movable fiber will introduce. According to this invention, however, the balancing is done on the beam that already has traversed the fiber and thus the changes in the transmission properties of the fiber or fiber bundle do not affect the measurement.

The method according to this invention also has the advantages of simplicity and relatively low cost, as only one detector is needed.

This invention is an improvement over the balanced two-wavelength method described in Harjunmaa also in that the background absorption of two matrix components can be balanced out simultaneously. The matrix constituents most significant in near-infrared non-invasive measurements on the human body are water and proteins. Using the new wavelengths according to this disclosure, the signal given by glucose in the three-component mixture water-protein-glucose is substantially independent of the relative concentrations of water and proteins. The new wavelength pair has the advantage of being simultaneously in balance with respect to water and most proteins. In other words, the absorption coefficient of water at these two wavelengths is the same, and the absorption coefficient of proteins at these same two wavelengths is the same, although different from the water absorption coefficient. Thus, changes in the relative concentrations of water and proteins, which are the two most important interfering substances present in animal tissue, do not affect greatly the reading of the instrument, which serves as an indication of glucose concentration in the tissue. These wavelengths are approximately 2155 and 2272 nm and may vary slightly according to the relative concentration of different proteins and also according to the temperature of the tissue. In the wavelength range concerned, the proteins that are present in the highest concentrations in the human body, hemoglobin, albumin and globulin, all have almost similar spectra.

The interfering substances present in the body, such as proteins, fats, cholesterol, etc., may, even after a careful wavelength selection, produce a residual signal due to their differential absorbance. Because of this, a personal calibration step is required before this system is used for glucose determination. The calibration is performed by taking a blood sample of the subject, determining its glucose content and, at the same time, performing a measurement according to this method. The signal obtained is recorded to correspond to the actual initial glucose concentration. The varying concentrations can then be later deduced by using the known sensitivity of this stem to glucose obtained by measuring glucose calibration samples.

If it is judged necessary to improve the specificity of the method, more than one wavelength pair can be used. If, for example, two wavelength pairs are used, the measurement can be done in a sequential mode, where a complete measurement is made according to this disclosure, first using one wavelength pair, and then the wavelengths are changed and another measurement is made with those wavelengths. It is also possible, although it may lead to a more complicated apparatus, to multiplex more than two wavelengths into one measuring beam and then to extract the information pertaining to each wavelength pair from the multiplexed signal. Also, if more than one wavelength pair is used, at least one of the wavelengths may be common to more than one pair.

Figure 2:
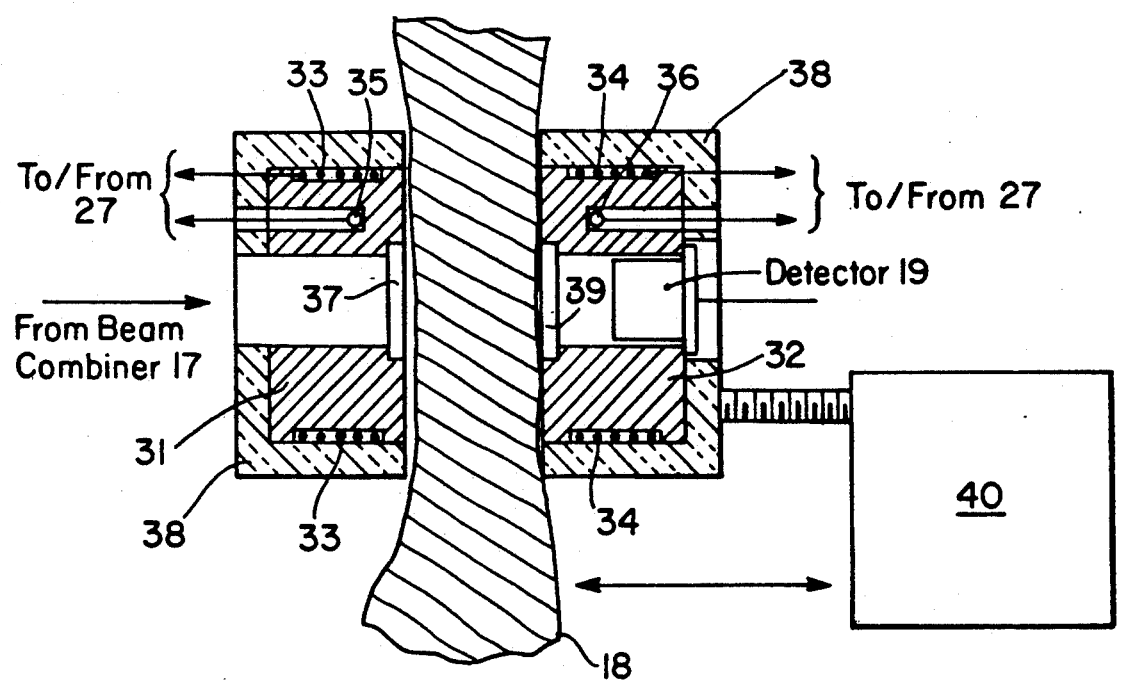
FIG. 2 is a schematic side view of a temperature-controlled variable gap mechanism for use in the apparatus of FIG. 1.

The temperature-controlled variable-gap mechanism 30 is depicted in detail in FIG. 2. It consists of two metal (for instance, aluminum) good heat conducting blocks or cylinders 31, 32 that incorporate heating resistors 33, 34, respectively. The temperature of the cylinders is sensed by temperature sensors 35 and 36, which feed back a control signal to the control unit 27. The control unit 27 adjusts the current through resistors 33 and 34 to maintain a predetermined constant temperature, near the normal body temperature. The sample 18, for instance the earlobe, is disposed between cylinders 31 and 32. The purpose of the hole in cylinder 31 is to allow the beam emerging from the beam combiner 17 to enter the sample through window 37. The cylinders are covered by low thermal conductance sheathing 38. Cylinder 32 is similar in structure to cylinder 31, except that detector 19 is installed behind window 39. Cylinder 32 can be moved along its axis using actuator 40 to vary the gap between windows 37 and 39.

Temperature variations that occur during the measurement will shift the water absorption spectrum features, causing erroneous differential absorption readings. For this reason, the preferred embodiment of this method includes a temperature control device 27 that maintains the variable gap mechanism at a known constant temperature which in turn keeps the part being squeezed 18 at a relatively constant temperature.

EQUIVALENTS

Those skilled in the art will recognize, or be able to ascertain, using no more than routine experimentation, many equivalents to the specific embodiments of the invention described herein.

These and all other equivalents are intended to be encompassed by the following claims. For example, other radiation sources, such as lasers, or light- or infrared-emitting diodes, are obviously also applicable, provided that the required wavelengths are available. Also, using appropriate modulation and filtering means, such as an acousto-optic tunable filter, one light source can be made to deliver the two-wavelength half-periods required.

The analyte may be a naturally occurring or homologous body material, such as glucose or cholesterol or a heterologous material or chemical, such as heavy metals, alcohol, nicotine or other drugs.

We claim:

1. A non-invasive method for measuring the concentration of analytes in living tissue containing fluids, comprising the steps of:
    a) illuminating the tissue with an electromagnetic beam comprised of alternate periods of monochromatic wavelengths, one of the alternate periods having a wavelength that is absorbed by the analyte, and the other alternate period having a wavelength selected so as to have an extinction coefficient in the tissue identical with that of the first wavelength;
    b) detecting the electromagnetic beam after reaction with the tissue to produce a first electrical signal;
    c) adjusting the intensity relation between wavelength periods of the illuminating beam so as to produce a substantially zero alternating component in the first electrical signal;
    d) varying the balance of analyte present in the tissue; and
    e) detecting an alternating component of the beam that has interacted with the tissue to generate a second electrical signal proportional to the concentration of analyte in the tissue; and
    f) calculating the concentration of the analyte in the tissue.

2. The method according to claim 1 where the residual amplitude of the alternating component, if there is any remaining after step (c), is recorded and used to calculate the concentration of the analyte.

3. The method according to claim 1 wherein varying the balance of analyte includes changing tissue thickness.

4. The method according to claim 3 wherein the tissue thickness change is substantially equal to the inverse of the extinction coefficient of the tissue at the wavelengths used.

5. The method according to claim 4 wherein the tissue thickness change is repeated cyclically, and the second electrical signal variation over the cycle is used as a measure of the concentration of the analyte in blood.

6. The method according to claim 1 wherein varying the balance of analyte is accomplished by the normal pulsatile cycle produced by the heart beat.

7. The method according to claim 1, whereby, before illuminating the sample with the electromagnetic beam, the tissue is illuminated by a radiation transmitting means with a pulsed beam containing only one of the two alternating wavelengths, and the radiation that has interacted with the sample is detected with a radiation detecting means to produce a third electrical signal.

8. The method according to claim 7 whereby at the beginning of the measurement, the thickness of the tissue between the radiation transmitting means and the radiation detecting means is decreased gradually until the amplitude of the transmitted radiation pulse train attains a predetermined value.

9. The method according to claim 7 whereby the third electrical signal is recorded and the second electrical signal obtained in step e) of claim 1 is normalized by dividing it by the third electrical signal.

10. The method according to claim 1 wherein the electromagnetic beam traverses the tissue.

11. The method according to claim 1 wherein the electromagnetic beam is reflected from the tissue.

12. The method according to claim 1 wherein the analyte is a heterologous material.

13. The method according to claim 1 wherein the analyte is a homologous material.

14. The method of claim 1 wherein the analyte is glucose and the alternate wavelengths are 2155 nm and 2272 nm.

15. A non-invasive apparatus for measuring the concentration of analytes in a living tissue, comprising:
    a) a source of electromagnetic radiation for illuminating the tissue with an electromagnetic beam comprised of alternate periods of different wavelengths, one of the alternate periods having a first wavelength that is absorbed by the analyte, and the other alternate period having a wavelength selected so as to have an extinction coefficient in the tissue identical with that of said first wavelength;
    b) a detector means for detecting the electromagnetic beam after reaction with the tissue to produce a first electrical signal proportional to the intensity of said electromagnetic beam; and
    c) intensity control means for adjusting the intensity relation between wavelength periods of the illuminating beam so as to produce, a reference level component in the first electrical signal when a minimum level of analyte is present in the tissue;
    d) whereby the first electrical signal when analyte is present is proportional to the concentration of analyte in the tissue.

16. The apparatus according to claim 15 wherein the radiation source comprises a master source and a slave source, each generating a beam of light which beams are combined to form said alternating periods of different wavelengths.

17. The apparatus according to claim 16 wherein the master source and slave source comprise incandescent lamps with filters for passing monochromatic light of different wavelengths $\lambda_1$ and $\lambda_2$.

18. The apparatus of claim 17 wherein $\lambda_1$ is 2155 nm and $\lambda_2$ is 2272 nm and the analyte is glucose.

19. The apparatus of claim 15 including means for changing tissue thickness to produce the minimal level of analyte in the tissue.

20. The apparatus according to claim 19 wherein the tissue thickness change is substantially equal to the inverse of the extinction coefficient of the tissue at the wavelengths used.

21. A non-invasive apparatus for measuring the concentration of analytes in a living tissue, comprising:
   a) a source of electromagnetic radiation for illuminating the tissue with an electromagnetic beam comprised of alternate periods of different wavelengths, one of the alternate periods having a first wavelength that is absorbed by the analyte, and the other alternate period having a wavelength selected so as to have an extinction coefficient in the tissue identical with that of said first wavelength;
   b) a detector means for detecting the electromagnetic beam after reaction with the tissue to produce a first electrical signal proportional to the intensity of said electromagnetic beam; and
   c) analyte level changing means for changing the level of analyte in the tissue;
   d) intensity control means for adjusting the intensity relation between wavelength periods of the illuminating beam so as to produce, a reference level component in the first electrical signal when a minimum level of analyte is present in the tissue whereby the first electrical signal when analyte is present is proportional to the concentration of analyte in the tissue;
   e) temperature control means for maintaining the temperature of the tissue substantially constant during measurement.

22. The apparatus according to claim 21 wherein the radiation source comprises a master source and a slave source, each generating a beam of light which beams are combined to form said alternating periods of different wavelengths and fiber optic means for transmitting the combined beam to the tissue.

23. The apparatus according to claim 22 wherein the master source and slave source comprise incandescent lamps with filters for passing monochromatic light of different wavelengths $\lambda_1$ and $\lambda_2$.

24. The apparatus of claim 23 wherein $\lambda_1$ is 2155 nm and $\lambda_2$ is 2272 nm and the analyte is glucose.

25. The apparatus of claim 21 wherein the analyte level changing means includes means for changing tissue thickness to produce the change in level of analyte in the tissue.

26. The apparatus of claim 21 wherein the temperature control means includes a pair of oppositely disposed thermally conductive bodies disposed opposite each other with a variable gap between them, into which gap the tissue is adapted to be placed and wherein the temperature of the bodies is sensed and controlled.

27. The apparatus of claim 26 including an opening through said bodies for passing the radiation beam through the tissue for detection.

28. The apparatus of claim 27 wherein the analyte level changing means comprises actuator means for moving one body relative to the other to squeeze said tissue.

* * * * *